United States Patent [19]

Borysko et al.

[11] Patent Number: 5,057,401
[45] Date of Patent: Oct. 15, 1991

[54] PROCESS FOR MAKING A DEVICE WITH A THREE-DIMENSIONALLY TAPERED POINT

[75] Inventors: Emil Borysko, Bridgewater; Daniel Hughes, Raritan, both of N.J.

[73] Assignee: Ethicon, Inc., Somerville, N.J.

[21] Appl. No.: 490,117

[22] Filed: Mar. 7, 1990

[51] Int. Cl.$^5$ .......................... G03C 5/00; B21G 3/18
[52] U.S. Cl. .................... 430/320; 430/323; 430/394; 163/4; 163/5
[58] Field of Search ...................... 430/320, 323, 394; 428/339; 163/4, 5, 7

[56] References Cited

U.S. PATENT DOCUMENTS

| | | | |
|---|---|---|---|
| 2,469,689 | 5/1949 | Gresham | 430/323 |
| 3,942,981 | 3/1976 | Sato | 430/322 |
| 4,587,202 | 5/1986 | Borysko | 430/320 |
| 4,711,800 | 12/1987 | DiVincenzo | 438/131 |
| 4,777,096 | 10/1988 | Borysko | 428/571 |

Primary Examiner—Charles L. Bowers, Jr.
Assistant Examiner—Thorl Chea
Attorney, Agent, or Firm—Matthew S. Goodwin

[57] ABSTRACT

Process for preparing a pointed device by a photochemical process by coating the top and bottom surfaces of a sheet material with a light-sensitive photoresist, exposing the photoresist with light through a light-impenetrable mask in the form of an image of the device shaped with a blunt end at the tip of the point to compensate for lateral etching during the etching step, said image on the top surface being slightly offset relative to the image on the bottom surface, further exposing with light a portion of the image of the point of the device on the top surface of the sheet material, said exposure conforming generally to a V-shaped configuration running along the inside perimeter of the point, removing exposed photoresist, and then contacting the treated sheet material with an etchant to remove material not protected by the remaining photoresist.

4 Claims, 3 Drawing Sheets

FIG-4
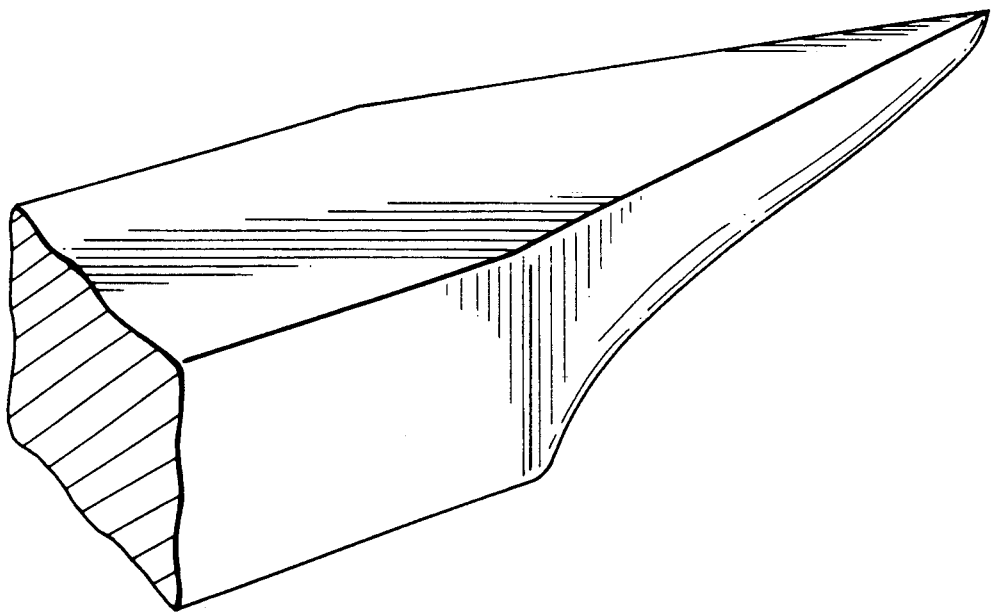
FIG-5 _PRIOR ART_
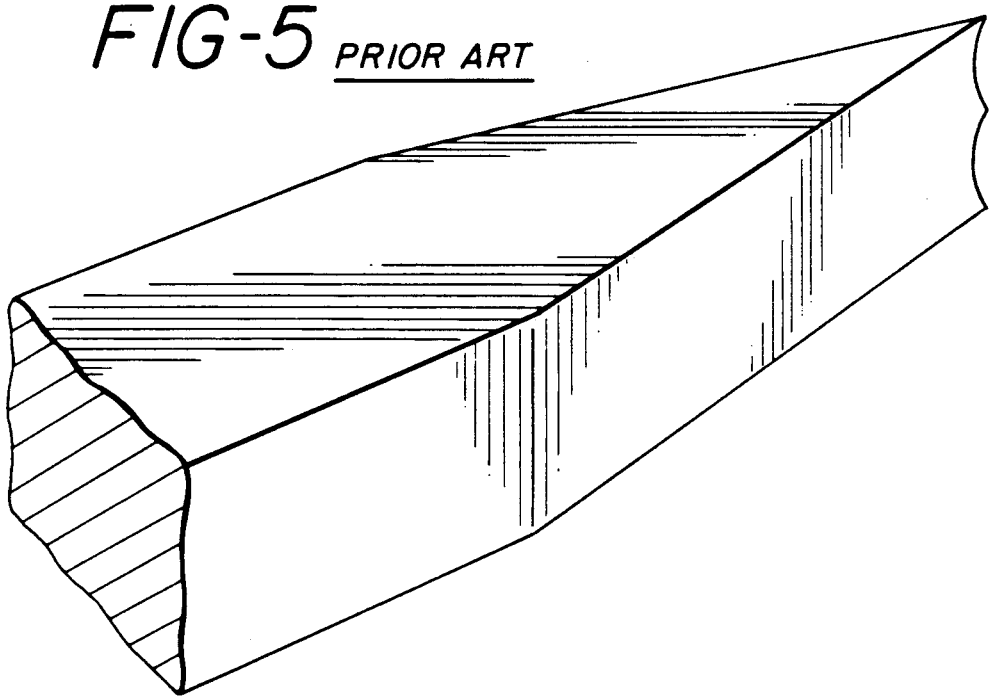

PROCESS FOR MAKING A DEVICE WITH A THREE-DIMENSIONALLY TAPERED POINT

BACKGROUND OF THE INVENTION

This invention relates to a photochemical process for making a device with a three-dimensionally tapered point suitable for needles, staples and other pointed devices.

Numerous pointed devices, such as surgical needles, are typically prepared one at a time by a multistep, labor-intensive process from stainless steel wire. U.S. Pat. Nos. 4,587,202 and 4,777,096 (Borysko patents) disclose an alternative process for preparing surgical needles without requiring the high degree of manual labor associated with conventional processes. A metal sheet exhibiting the properties desired for a surgical needle is first coated on at least one surface with a light-sensitive photoresist, preferably on both the top and bottom surfaces thereof, and then the coated surfaces are exposed to light in the form of an image of a plurality of surgical needles where each needle is shaped with a square blunt end to compensate for lateral etching which occurs during a later etching step. The image of the needles is typically prepared by covering the coated metal sheet with a negative or photomask. The photomask contains a light-impenetrable mask shaped in the form of the surgical needles, so that when the sheet is exposed to light, an image of the needles is created on the coated surface corresponding to the shape of the light-impenetrable mask. The exposed photoresist is removed and unwanted metal not protected by the remaining photoresist is etched away in an etching solution. In the preferred process, the images of the surgical needles for the top and bottom surfaces of the metal sheet are mirror images of each other precisely superimposed. After removing the photoresist from the needles prepared, the needles can be electropolished, attached to sutures, and then sterilized for surgical applications. This process affords an alternative to the slow mechanical production of surgical needles one at a time, and reduces the manpower and therefore the overall cost of preparing such needles.

Unfortunately, the needles produced by the Borysko patents have points terminating with chisel-shaped tips which resist penetration and may tear tissue during surgical procedures. In view of this problem, it would be desirable to improve upon this process so that a symmetrical three-dimensionally tapered point having the ability to easily penetrate tissue or other material can be prepared by a photoetching process.

SUMMARY OF THE INVENTION

The invention is an improved process for preparing a device having a point with a tip, although the process is applicable for the preparation of a plurality of devices simultaneously having not only one point, but also, if desired, two or more points. The process is an improvement of the process disclosed in the Borysko patents, which generally disclose coating the top and bottom surfaces of a sheet material exhibiting the properties desired for the device with a light-sensitive photoresist, exposing the photoresist with light through a light-impenetrable mask wherein said mask is in the form of an image of the device shaped with a blunt end at the point to compensate for lateral etching during the etching step, said images for the top and bottom surfaces of the sheet material being mirror images of each other in precise register, removing the exposed photoresist and contacting the treated sheet material with an etchant to remove material not protected by the remaining photoresist. The improvement comprises the following steps: a) shortening the length of the image of the point of the device on the top surface of the sheet material relative to the length of the image of said point on the bottom surface thereof so as to offset the images of the point of the device on the top and bottom surfaces of the sheet material relative to each other; and b) exposing with light a portion of the image of the point of the device on the top surface of the sheet material with a V-shaped configuration disposed generally along the perimeter of said point and running substantially parallel to each side of said point to the blunt end of the tip of the point so as to form an apex in close proximity to said blunt end and axially aligned with the longitudinal axis of said point.

The improved process of this invention enables the skilled artisan to produce a device having a long, three-dimensionally tapered point. Examples of such devices which can be prepared by the process of this invention include needles for the textile industry, such as knitting needles, surgical needles, staples and clips. These pointed devices can easily penetrate tissue or other materials and reduce the risk of tearing tissue or other materials during their intended use. Additionally, the shape and length of the taper can be adjusted by varying the dimensions of the V-shaped configuration and the amount of offset of the top and bottom images of the point.

BRIEF DESCRIPTION OF THE DRAWINGS

FIG. 4 is an enlarged perspective view of a portion of a surgical needle which can be prepared by the process of this invention.

FIG. 5 is an enlarged perspective view of a portion of a surgical needle prepared by the prior art process disclosed in the Borysko patent.

DETAILED DESCRIPTION OF THE INVENTION

The photoetching process of U.S. Pat. Nos 4,587,202 and 4,777,096 (Borysko patents), incorporated by reference herein, describe the general procedures and operating conditions required to produce the surgical needle of this invention. The Borysko patent describes the preparation of a plurality of surgical needles from a single metal sheet, and obviously, the improved process of this invention is not only applicable to the production of a single needle but also preferably to the production of numerous needles from a single photoetching process. Additionally, the process described in the Borysko patents can be used for preparing other pointed devices such as staples and clips. The pointed devices can be prepared by photoetching not only a metal sheet, but also other photoetchable sheet materials such as polymers, ceramics, or any other sheet material having suitable properties. Preferably, the sheet material is a metal sheet.

For purposes of describing this invention, the top and bottom surfaces of the sheet material are the two surfaces which are parallel to the plane of the sheet thereof. The point of a device is that portion of the device running generally from the pointed tip to the maximum width of the device, and the length of the point refers to the measured dimension in a direction parallel to the longitutinal axis of the point. A taperpoint device, e.g. a taperpoint needle, refers generally to those devices whose points taper from the maximum diameter of the device to a sharp, symmetrical tip. For certain devices, such as staples, the device may have two or more points.

As described in the Borysko patents, the photoresist-treated sheet material is covered with a photomask to selectively control those areas of the sheet upon which the contact of light is desired. The photomask contains a light-impenetrable mask shaped in the form of an image of the pointed device with a blunt end at the tip. In the Borysko process, the photomask for the top surface of the sheet material is the mirror image of the photomask for the bottom surface, and in perfect registry therewith.

In the improved process of this invention, the top and bottom photomasks are not mirror images. The length of the image of the point of the device for the top surface of the sheet material is reduced, thereby offsetting the images contained in the photomasks for the bottom and top surfaces of the sheet material relative to each other. Additionally, a V-shaped configuration of light is exposed through the light-impenetrable mask of the image of the pointed device for the top surface of the metal sheet. The V-shaped configuration is disposed inside the perimeter of the image of the point. The exposure of light in the V-shaped configuration can be conveniently accomplished when the photomask for the sheet material is prepared. Such a V-shaped configuration is not present in the photomask for the bottom surface of the sheet material.

Figure 1:
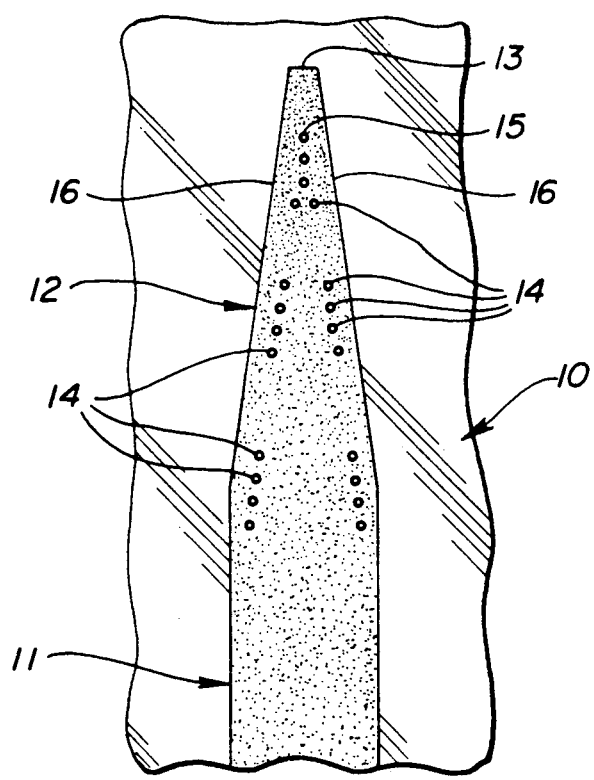
FIG. 1 is an enlarged plan view of a portion of a photomask image for the top surface of a sheet which can be used in carrying out the process of this invention.

Referring now to the specific embodiments illustrated in the drawings, FIG. 1 shows a portion of a photomask 10 for the top surface of a sheet. The photomask 10 depicts a portion of a needle with a body 11 and a point 12, extending to a blunt end 13 at the tip.

In one embodiment, the V-shaped configuration is provided by a plurality of light transmittant apertures or holes 14 running generally along the perimeter of the point 12 and running parallel to the sides 16 of the point 12 so as to form an apex 15 in close proximity to the blunt end 13 and parallel to the longitudinal axis of the point 12.

Figure 2:
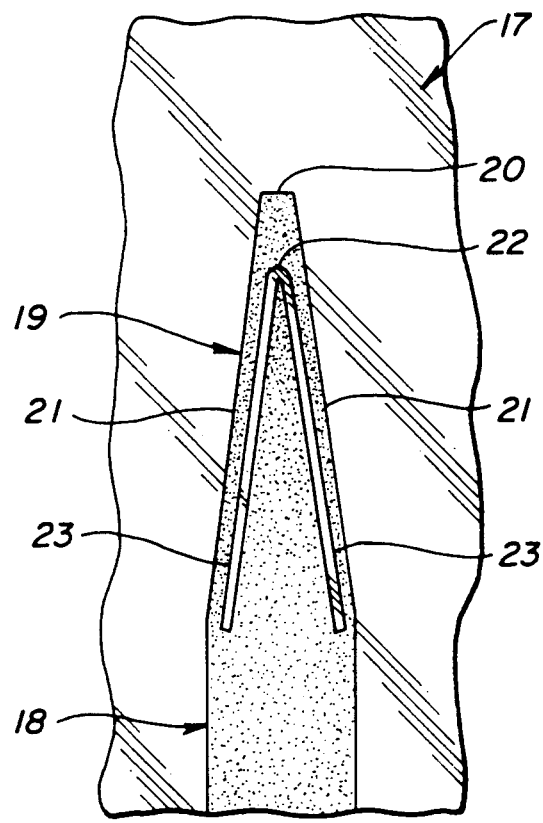
FIG. 2 is an enlarged plan view of a portion of an alternative photomask image for the top surface a sheet which can be used in carrying out the process of this invention.

In another embodiment as shown in FIG. 2, a portion of photomask 17 for the top surface of a metal sheet depicts a needle body 18 and point 19 extending to blunt end 20. The V-shaped configuration 23 is depicted as two slits each running parallel to the sides 21 of the point 19 thereby forming an apex 22 in close proximity to blunt end 20 and parallel to the longitudinal axis of the point 19.

Figure 3:
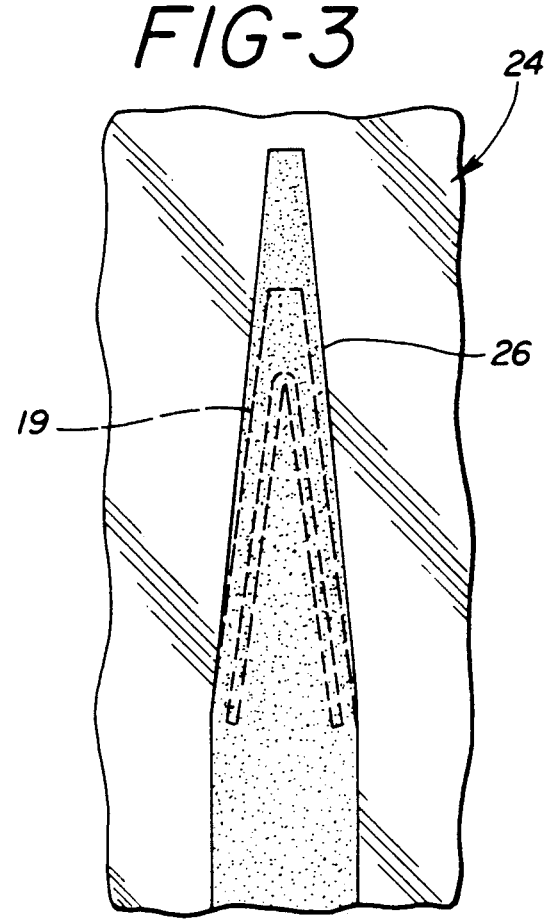
FIG. 3 is an enlarged plan view of the photomask image shown in FIG. 2 superimposed on a portion of a photomask image for the bottom surface of the sheet.

FIG. 3 depicts the photomask of FIG. 2, shown by dotted lines, superimposed on the identical portion of the photomask 24 for the bottom surface of the sheet. The length of the point 26 for the bottom surface is longer than the length of the point 19 for the top surface, thereby offsetting the photomask images on each surface relative to each other.

The shape of the point can be varied significantly to prepare pointed devices with shapes particularly suited for specific applications by varying not only the length, width and other dimensions of the image of the point itself on the top surface of the sheet material, but also the positioning and the dimensions of the V-shaped configuration.

Figure 6:
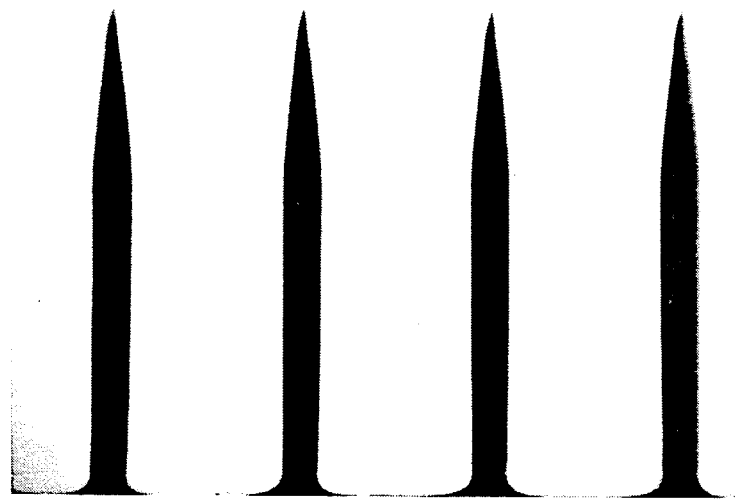
FIG. 6 is a photomicrograph in plan view of four surgical needles magnified 100 times prepared by the process of this invention.

FIGS. 4 and 5 illustrate the dramatic improvement in the shape of a needle point prepared by the process of this invention when compared to a needle point prepared by the prior art process described in the Borysko patents. Unlike the point prepared by the process of this invention as seen in FIG. 4, which tapers to a sharp tip, the needle prepared according to the Borysko patent as seen in FIG. 5 has a rough, chisel-shaped tip with a number of ridges that could potentially tear tissue during operative procedures. The photograph shown in FIG. 6 dramatically illustrates the long taper and sharp, symmetrical tip of needles when prepared according to the improved process of this invention.

After a treated metal sheet is etched for the preparation of a surgical needle, the photoresist can be removed from the needle using conventional techniques. The needle can then be electropolished, swaged or fastened to one or more sutures if desired, and then sterilized to prepare a needle suitable for numerous surgical applications. Similarly, desired processing steps can be performed for other pointed devices once the photochemical process is completed.

As described in the Borysko patents, although the invention is illustrated in terms of a dry positive photoresist technique, it is possible to carry out the process of this invention using other types of photoresists.

What is claimed is:

1. In a process for preparing a device having a point with a tip of the type wherein a sheet material exhibiting the properties desired for the device is coated on the top and bottom surfaces thereof with a light-sensitive photoresist, the photoresist is exposed with light through a light-impenetrable mask wherein said mask is in the form of an image of the device shaped with a blunt end at the tip of the point to compensate for lateral etching during the etching step, said images for the top and bottom surfaces of the sheet material being mirror images of each other, the exposed photoresist is removed and the treated sheet material is contacted with an etchant to remove material not protected by the remaining photoresist; the improvement comprising the steps of:

a) shortening the length of the image of the point of the device on the top surface of the sheet material relative to the length of the image of said point on the bottom surface thereof so as to offset the images of the point of the device on the top and bottom surfaces of the sheet material relative to each other; and b) exposing with light a portion of the image of the point of the device on the top surface of the sheet material with a V-shaped configuration disposed generally along the perimeter of said point and running substantially parallel to each side of said point to the blunt end of the tip of the point so as to form an apex in close proximity to said blunt end and axially aligned with the longitudinal axis of said point.

2. The process of claim 1 wherein the V-shaped configuration is in the form of a plurality of holes extending generally parallel to the sides of the point.

3. The process of claim 1 wherein the V-shaped configuration is in the form of two narrow slits, each slit extending generally parallel to a side of the point.

4. The process of claim 1 wherein the photoresist is exposed with light through a light-impenetrable mask in the form of an image of a plurality of pointed devices.

* * * * *